(12) United States Patent
Mills et al.

(10) Patent No.: US 7,131,994 B2
(45) Date of Patent: *Nov. 7, 2006

(54) MUSCLE-BASED GRAFTS/IMPLANTS

(75) Inventors: C. Randal Mills, Tioga, FL (US); John R. Bianchi, Gainesville, FL (US); Michael R. Roberts, Gainesville, FL (US); David T. Cheung, Arcadia, CA (US); Chandrasekaran Nataraj, Gainesville, FL (US); John W. Howell, Jr., Gainesville, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/793,976

(22) Filed: Mar. 5, 2004

(65) Prior Publication Data
US 2005/0152881 A1    Jul. 14, 2005

Related U.S. Application Data

(63) Continuation-in-part of application No. 10/754,310, filed on Jan. 9, 2004, now Pat. No. 7,001,430.

(51) Int. Cl.
*A61F 2/08* (2006.01)
*A61K 35/34* (2006.01)
*A61K 38/17* (2006.01)

(52) U.S. Cl. .................. 623/14.13; 424/423; 424/548; 514/12

(58) Field of Classification Search ............. 623/14.13; 424/423, 548; 514/12
See application file for complete search history.

(56) References Cited

U.S. PATENT DOCUMENTS

| 3,855,196 A | 12/1974 | Matsukawa et al. |
| 6,659,995 B1 | 12/2003 | Taheri |
| 2002/0119177 A1 | 8/2002 | Bowman et al. |
| 2003/0113301 A1* | 6/2003 | Edge et al. .............. 424/93.21 |
| 2003/0180266 A1 | 9/2003 | McKay et al. |

FOREIGN PATENT DOCUMENTS

| WO | WO 96/39035 A | 12/1996 |
| WO | WO 01/78754 A | 10/2001 |

OTHER PUBLICATIONS

Djurhuus et al., "Methodological aspects of measuring human skeletal muscle electrolyte content and ouabain binding capacity," Anal Biochem 260:218-222, 1998.*

(Continued)

*Primary Examiner*—Robert A. Wax
*Assistant Examiner*—Rosanne Kosson
(74) *Attorney, Agent, or Firm*—Donald J. Pochopien; McAndrews, Held & Malloy

(57) ABSTRACT

The present invention is directed to a composition comprising a matrix suitable for implantation in humans, comprising defatted, shredded, allogeneic human muscle tissue that has been combined with an aqueous carrier and dried in a predetermined shape. Also disclosed is a tissue graft or implant comprising a matrix suitable for implantation in humans, comprising defatted, shredded, allogeneic human muscle tissue that has been combined with an aqueous carrier and dried in a predetermined shape. The composition and/or tissue graft or implant of the invention is usable in combination with seeded cells, a tissue growth factor, and/or a chemotactic agent to attract a desired cell.

35 Claims, 4 Drawing Sheets
(4 of 4 Drawing Sheet(s) Filed in Color)

OTHER PUBLICATIONS

Journal of Bone and Mineral Research, Apr. 2003, vol. 18, No. 4, p. 705, "In Vitro and In Vivo Synergistic Interactions Between the Runx2/Cbfa1 Transcription Factor and Bone Morphogenetic Protein-2 in Stimulating Osteoblast Differentiation", Shuying Yang, Daoyan Wei, Dian Wang, Mattabhorn Phimphilai, Paul H. Krebsbach and Renny T. Franceschi.

Djurhuus M S et al.: "Methodological aspects of measuring human skeletal muscle electrolyte content and ouabain binding capacity." Analytical Biochemistry. Jul. 1, 1998, vol. 260, No. 2., Jul. 1, 1998, pp. 218-222, XP002296843 ISSN: 0003-2697.

Yang et al, "In Vitro and in vivo synergistic interactions between the Runx2/Cbfal ranscription factor and bone morphogenetic protein-2 in stimulating osteoblast differentiation", J Bone Mineral Res 18 (4) : 705-715, 2003.

* cited by examiner

MUSCLE-BASED GRAFTS/IMPLANTS

BACKGROUND OF THE INVENTION

This application is a continuation-in-part of U.S. Ser. No. 10/754,310, filed Jan. 9, 2004, now U.S. Pat. No. 7,001,430.

The present invention is directed to the field of biocompatible matrices for use in forming devices for implantation in animals and humans. More particularly, the present invention is directed to an implantable composition or a tissue graft/implant formed from an allogeneic biocompatible human muscle matrix that is capable of carrying other implantable materials or that can be formed into a plurality of tissue implants or compositions having different properties and different shapes. The present invention is useful because it provides an implantable composition or device that is versatile in its ability to be formulated into a variety of implants or grafts that are useful in the treatment of a variety of medical conditions in patients.

In the field of biomedical implants, devices have been made that range far afield from the biological components found in the human body. For example, many devices that are intended as bone substitutes are made from metals such as titanium, or biocompatible ceramics. A problem in such instances is that they have different material properties than the host tissue causing the devices to loosen at the interface between the host tissue and the device itself.

One solution to the problem was the use of allograft bone in place of metal or ceramic implants. Under the proper conditions and under the influence of osteogenic substances, implants made of allograft bone can act as the scaffolding for remodeling by the host. Such implants function by being both structurally and biologically similar to the host tissue. Further, they allow cellular recruitment through the natural openings in the matrix and allow the graft to be replaced by natural host bone. While allograft bone is very useful, it is limited by the intended clinical use. Thus, it is particularly useful for spinal fusions where the spacings between the vertebrae are relatively fixed and well known. However, injuries come in a variety of shapes and sizes that present a logical limitation on the availability of an ideal graft to fill the defect. Moreover, availability, donor demographics and cost further limit the usefulness of allograft bone. Accordingly, there is a need in the art for an implantable biocompatible matrix that can be formulated into a variety of shapes and sizes and that can act as scaffolding to allow the infiltration of native regenerative cells that will lay down a natural replacement structure in the shape of the implant.

Another example area where biocompatible implants are important is in replacement skin for burn victims. Histocompatibility, remodeling and safety are considerable problems in utilizing allograft skin. To avoid this problem and the shortage of viable donor skin, a surgeon often removes skin from another part of the patient and transplants it to the area of need. While such skin is non-antigenic, it causes significant morbidity to the patient at the site of removal. Moreover, depending upon the size of the wound or burn, there may not be sufficient skin on the patient to satisfy the need. To alleviate this problem, at least one company will culture the patient's skin cells on a collagen matrix to form a transplantable layer of skin. However, the culture time is relatively extensive and the patient's wound or burn is exposed while awaiting the graft. Moreover, the grafts generated in this way do not mimic normal skin, which is composed of multiple cell types and structures. Accordingly, there is a need in the art for an implantable biocompatible matrix that can be formulated into a sheet and cut to size and that can act as scaffolding to allow the infiltration of a variety skin cells from adjacent tissue that will lay down a compatible and natural replacement structure in the shape of the implant, while absorbing the implant itself.

It is an object of the present invention to prepare a matrix from biological tissue that has the ability to be formulated into a variety of forms and shapes that can participate in the correction of a variety of pathologies such as those described above.

SUMMARY OF THE INVENTION

The applicants have discovered a composition that provides a biocompatible, non-antigenic matrix and scaffolding material for tissue regeneration in humans. In its simplest form, the present invention is directed to a composition comprising a matrix suitable for implantation in humans, comprising defatted, shredded, allogeneic human muscle tissue that has been combined with an aqueous carrier and dried. Typically, the composition of the present invention is sufficiently dried to so as to be able to be handled. More typically, it is dried to a moisture content of about 3% or less.

In another aspect, the present invention is directed to a tissue graft/implant suitable for implantation in humans comprising a matrix of defatted, shredded, allogeneic human muscle tissue that has been combined with an aqueous carrier and dried in a predetermined shape. Typically, the shape of the tissue graft/implant of the present invention includes a strip, a sheet, a disc, a molded 3D shaped object, a plug, a sponge, and a gasket. Typically, the composition of the present invention is sufficiently dried to so as to be able to be handled. More typically, it is dried to a moisture content of about 3% or less.

Any human muscle is suitable for use in the compositions or tissue graft/implant of the present invention, including smooth muscle and striated muscle. Preferably, the human muscle tissue that is employed is striated muscle, such as skeletal muscle or cardiac muscle. More preferably, the muscle tissue employed is skeletal muscle tissue.

Any of the compositions of tissue graft/implants of the present invention may include collagen fibers, growth factors, antibiotics, cells, or particles such as demineralized bone matrix (DBM), mineralized bone matrix, cortical cancellous chips (CCC), crushed cancellous chips, tricalcium phosphate, hydroxyapatite, or biphasic calcium phosphate (wherein the latter is the combination of tricalcium phosphate and hydroxyapatite) or a combination thereof.

A composition or tissue graft/implant of the present invention that is particularly suited for treating bone trauma, bone disease or bone defects, for providing artificial arthrodeses, or for other treatment where new bone formation is desired, further comprises particles of DBM, mineralized bone matrix, CCC, crushed cancellous chips, tricalcium phosphate, hydroxyapatite, or biphasic calcium phosphate dispersed in the matrix.

A preferred composition or tissue graft/implant of the present invention that is particularly suited for treating bone trauma, bone disease or bone defects, for providing artificial arthrodeses, or for other treatment where new bone formation is desired, further comprises particles of DBM, mineralized bone matrix, CCC, crushed cancellous chips, tricalcium phosphate, hydroxyapatite, or biphasic calcium phosphate dispersed in the matrix, in combination with a therapeutically effective amount of a growth factor selected from the group consisting of bone morphogenic protein (BMP), LIM mineralization protein (LMP) and RUNX-2.

A preferred growth factor is BMP. BMP is a well-known naturally occurring bone protein and may be obtained by extraction from fresh bone. Methods for isolating BMP from bone are described in U.S. Pat. No. 4,294,753 to Urist and Urist et al., PNAS 371, 1984. Often BMP is obtained by packing fresh fragments of bone into a cavity in an implant that is designed for receiving such packing. However, the amount of BMP in such packing is variable. Therefore, it is preferred that the BMP be a recombinant human BMP such that its activity is known. Recombinant human BMPs are commercially available or prepared as described and known in the art, e.g., in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al., all of which are hereby incorporated herein by reference in their entirety. Recombinant human BMP-2 (rhBMP-2), recombinant human BMP-4 (rhBMP-4), recombinant human BMP-7 (rhBMP-7) or heterodimers thereof are more preferred. rhBMP-2 is most preferred.

The amino acid sequence of the RUNX-2 protein and vectors suitable for expressing the protein are disclosed in co-pending patent application U.S. Ser. No. 10/437,171, filed May 13, 2003, and incorporated herein in its entirety.

Other suitable tissue growth factors for use in combination with the composition and with the tissue graft/implant of the present invention include transforming growth factor-β(TGF-β), a fibroblast growth factor (FGF) such as FGF-1 to FGF-12, platelet-derived growth factor (PDGF), and insulin-like growth factor (ILGF). All of these factors are well known in the art.

The composition and the tissue graft/implant of the present invention comprise a matrix that is formed from the fibers of defatted, shredded, allogeneic human muscle tissue. This fibrous structure is advantageous because the resulting matrix that is formed is porous and particularly well suited both for the infiltration by colonizing cells (e.g., osteoconduction), and for the storage and slow release of seeded cells, growth factors (as described above), and chemotactic agents to attract desired cells (e.g., osteoinduction).

Thus, it is also within the scope of the present invention that the composition or implant/tissue graft of the present invention be combined with seeded cells, a tissue growth factor, or a chemotactic agent, or a combination thereof.

When the composition or tissue graft/implant of the present invention is to be used as a tissue graft for skin, it is optionally seeded with dermatocytes, more typically with dermatocytes and melanocytes.

When the composition or tissue graft/implant of the present invention is to be used to treat bone trauma, disease and defects, for artificial arthrodeses and for other treatment where new bone formation is desired, it is optionally seeded with osteogenic cells. Preferably, the composition or tissue graft/implant of the present invention is seeded with stem cells that will provide a natural distribution of the native cells necessary for restoration of the injury or defect at the site of implantation.

The tissue grafts and implants of the present invention exhibit a great degree of tensile strength. They are readily stitchable and retain a majority of their tensile strength even when rehydrated. In addition, upon hydration, tissue grafts and implants of the present invention are moldable and suitable for filling in irregular gaps or holes in the tissue to be repaired. Typically, the hydrated tissue is press fitted by the surgeon into the defect or cavity to be filled.

It is also within the scope of the present invention that the tissue graft/implant of the present invention be utilized with a load-bearing member used in a spinal fusion. Suitable load bearing members include hollow spinal cages, hollow dowels, C-shaped and D-shaped spacers and other devices known in the art, having a pocket, chamber or other mechanism for retaining the tissue graft/implant of the present invention. Typically, the load-bearing member has a compressive strength of at least about 1,000 N. More typically, when utilized between lumbar vertebrae, the load-bearing member has a compressive strength of 3,000 to 11,000 N. When utilized between cervical vertebrae, the load bearing member has a compressive strength of about 1,000 to 3,000 N. Suitable load bearing members are known in the art and described in multiple U.S. patents, including, for example in U.S. Pat. Nos. 5,522,899, 5,785,710, 5,776,199 and 5,814,084, 6,033,438, 6,096,081, each of which is hereby incorporated by reference in its entirety It was unexpectedly discovered that the skeletal muscle-based implantable devices and compositions of the present invention have hemostatic action and cause platelet activation. This is a particular advantage during surgical procedures wherein patient bleeding is a well known problem.

In its second aspect, the present invention is directed to a method for making a (muscle-based) composition or a tissue implant suitable for treating an injury or a surgical or medical condition in a human patient, wherein the tissue implant comprises a matrix of allogeneic human muscle. In this embodiment, the method comprises the steps of:
  i. removing the fat and soluble proteins from allogeneic or xenogeneic mammalian muscle tissue;
  ii. lyophilizing the muscle tissue from step (i);
  iii. shredding the lyophilized muscle tissue;
  iv. mixing the shredded muscle tissue in an aqueous carrier to form a muscle tissue slurry having a viscosity within the range of 1 centistoke to 20,000 centistokes;
  v. transferring the muscle tissue slurry to an appropriate shaped mold; and
  vi. drying the slurry in the mold to form the correspondingly shaped tissue implant.

In the above method, the matrix of allogeneic human muscle comprises from about 1% to about 100% of the final weight of the composition or implant, more typically from 50% to about 99% of the final weight of the implant, even more typically from 75% to about 99% of the final weight of the implant.

In another embodiment, the method of making a composition or tissue implant of the present invention further comprises combining the allogeneic human muscle with a demineralized bone matrix (DBM), cortical cancellous chips (CCC), tricalcium phosphate, hydroxyapatite, or biphasic calcium phosphate and/or shredded allogeneic human tendon. The addition of any of these components increases the viscosity of the intermediate slurry. When the tissue implant of the present invention contains DBM, mineralized bone matrix, CCC, crushed cancellous chips, tricalcium phosphate, hydroxyapatite, or biphasic calcium phosphate or a combination thereof, the resulting tissue implant is osteogenic and particularly suited for repairing bone. The implant of this embodiment also exhibits improved dimensional stability and ability to hold shape during drying, rehydration and handling. In one variation of the above embodiment, the DBM, mineralized bone matrix, CCC, crushed cancellous chips, tricalcium phosphate, hydroxyapatite, or biphasic calcium phosphate or a combination thereof are dispersed equally or randomly throughout the matrix. In another variation, the DBM, mineralized bone matrix, CCC, crushed cancellous chips, or a combination thereof are sandwiched between layers of the matrix to form a laminate implant. In either of the above referenced embodiments, the DBM, mineralized bone matrix, CCC, crushed cancellous chips, tricalcium phosphate, hydroxyapatite, or biphasic calcium phosphate or a combination thereof typically constitute from 1% to 99%, more typically 50% to 99%, most typically from 90% to 99% of the dry weight of the composition or implant.

When the tissue implant contains tendon, it is tougher, and stronger than the digested human muscle matrix alone and is particularly suited as a dressing for a wound or burn that will become infiltrated with skin cells and allow for development of a replacement skin layer that will cover the wound or burn. The ratio of tendon to intermediate composition ranges from 1:99 to 99:1 by dry weight. Typically, the range is 10:90 to 90:10; more typically, the range is 25:75 to 75:25. While the above discussion is in relation to "tendon," which is a preferred source of collagen for this invention, it is intended that any collagen source be used, including fascia, ligament, or dermis.

After the mixing step, the resulting intermediate composition (the digested allogeneic human muscle slurry) of the present invention is optionally degassed, by pouring the slurry into plates or tubes, and centrifuging them to eliminate any entrapped air and produce a higher density slurry.

Alternatively, the slurry is poured into a mold for formation of an implantable tissue matrix of any size or shape. As noted above, the slurry can be combined with other agents, such as DBM, CCC or a collagen (e.g., tendon, fascia) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable film or shape is then ready for packaging and final sterilization.

Prior to implantation, the freeze dried composition, tissue graft or implant of the present invention is removed from its sterile packaging and rehydrated by contacting with water, saline, blood, plasma, a buffered solution, or any other suitable liquid. Preferably, the rehydrating liquid contains a growth factor or a chemotactic agent as discussed above.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 3A. is a side view. In FIG. 3B, the implant is rotated 90° to show the hole that was molded in the center.

In FIG. 4A, the film was formed from the muscle slurry without an additive. In FIG. 4B, the film was made from a mixed slurry comprising a 50:50 ratio of muscle tissue to tendon tissue.

DETAILED DESCRIPTION OF THE INVENTION

Figure 1:
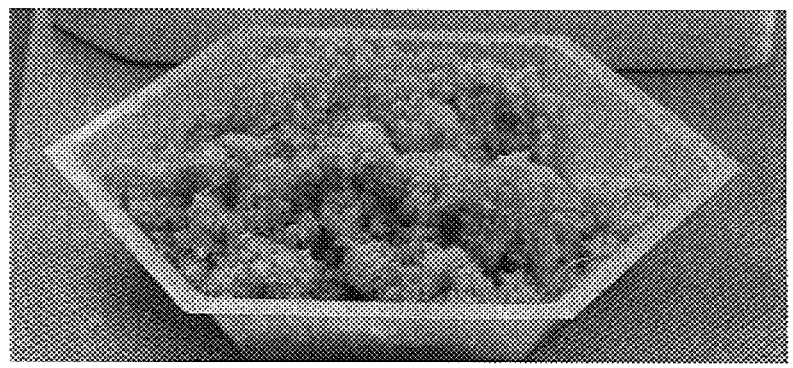
FIG. 1 is a photograph showing the fluffy fibrous texture of shredded, defatted allogeneic human muscle for use in making the intermediate composition (muscle slurry) of the present invention.
Figure 2A:
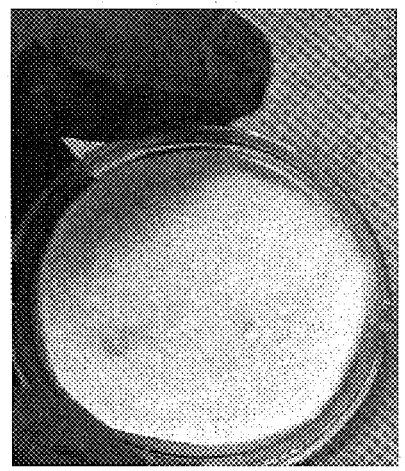
FIGS. 2A–2C are photographs of tissue implants in the form of a sponge that were made from the muscle slurry of the present invention.
Figure 2B:
Figure 2C:
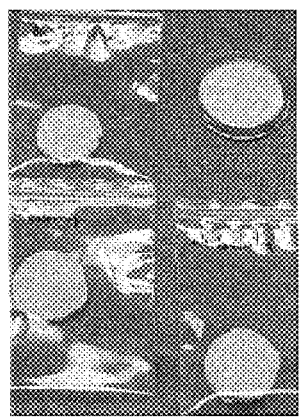
Figure 3A:
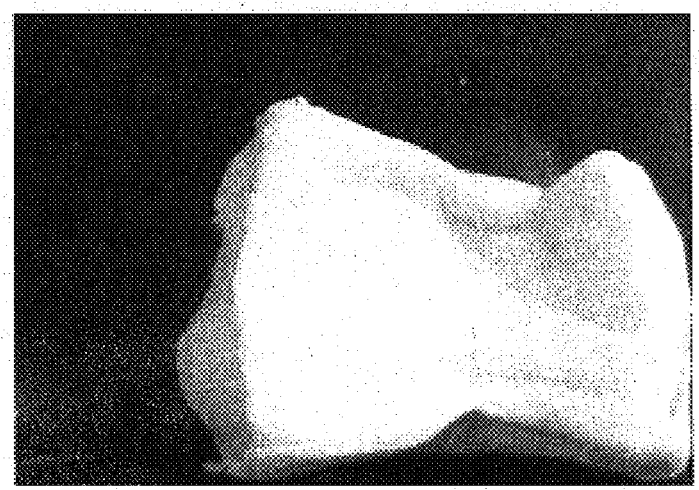
FIGS. 3A–3B are photographs of a three-dimensional molded tissue implant made from the muscle slurry of the present invention.
Figure 3B:
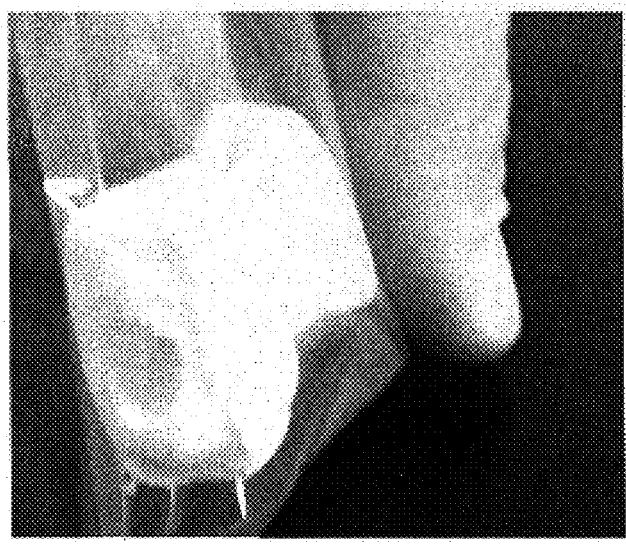
Figure 4A:
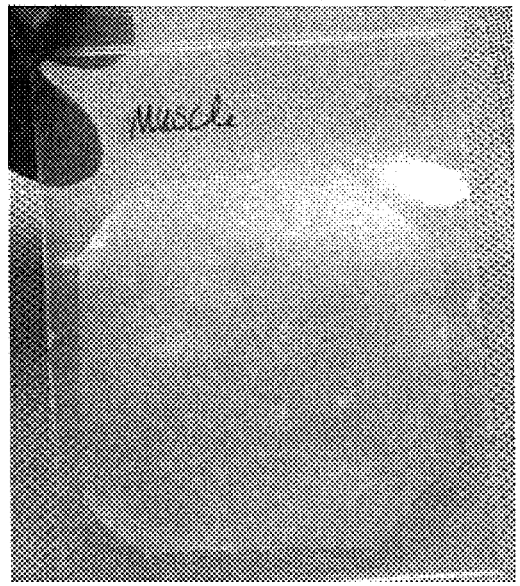
FIGS. 4A and 4B are photographs of tissue implants/grafts in the form of a thin film that were made from the muscle slurry of the present invention.
Figure 4B:
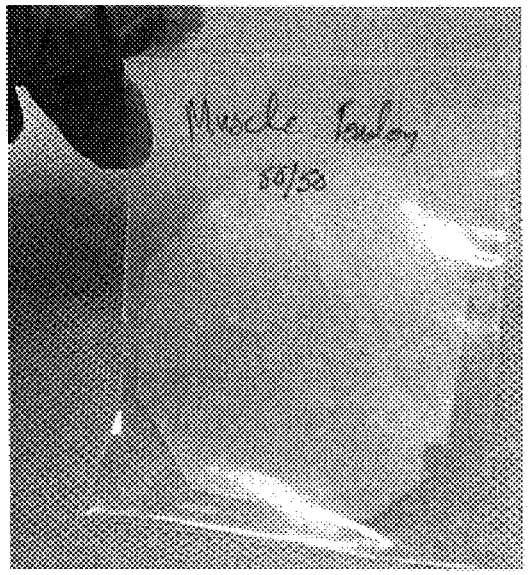

The present invention has multiple embodiments. In its first embodiment, the present invention is directed to a composition that provides a biocompatible, non-antigenic matrix and scaffolding material for tissue regeneration in humans. More specifically, the present invention is directed to a composition comprising a matrix suitable for implantation in humans, comprising defatted, shredded, allogeneic human muscle tissue that has been combined with an aqueous carrier and dried. Typically, the composition of the present invention is sufficiently dried to so as to be able to be handled. More typically, it is dried to a moisture content of about 3% or less.

To be suitable for implantation in humans, the composition (and implants) of the present invention must be treated to remove any antigenic proteins, which may generate a rejection of the implant. It also must be treated to remove any bacteria and viruses. Suitable processes for removing antigenic proteins and sterilizing to neutralize any bacteria and viruses are known in the art. See U.S. Pat. No. 5,846,484, entitled "Pressure flow system and method for treating a fluid permeable workpiece such as a bone," which issued to Scarborough, et al. on Dec. 8, 1998. In the present case, the applicants utilized the assignees' well known method for defatting tissue, which also has the added benefit of removing blood, cellular debris, and soluble and antigenic proteins, by subjecting the muscle tissue to alternating cycles of pressure and vacuum in the sequential presence of solvents, such as isopropyl alcohol, hydrogen peroxide and a detergent. These assignee's processes also neutralize any bacteria and viruses. These processes are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety.

In its second aspect, the present invention is directed to a tissue graft/implant suitable for implantation in humans comprising a matrix of defatted, shredded, allogeneic human muscle tissue that has been combined with an aqueous carrier and dried in a predetermined shape. The tissue graft/implant of the present invention is made in various shapes including that of a strip, a sheet, a disc, a molded 3D shaped object, a plug, a sponge, and a gasket. A preferred shape is a sponge. Any of these objects may include a cavity, a pouch, a hole, a post, a hook, or a suture. Any of these objects may be made with or without the addition of demineralized bone matrix (DBM), mineralized bone matrix, cortical cancellous chips (CCC), crushed cancellous chips, lyophilized and shredded muscle or collagen fibers, growth factors, antibiotics, stem cells, or other additives.

Preferably, the human muscle tissue that is employed in the composition and tissue graft/implant of the present invention is striated muscle, such as skeletal muscle or cardiac muscle, more preferably, skeletal muscle tissue.

A composition or tissue graft/implant of the present invention that is particularly suited for treating bone trauma, bone disease or bone defects, for providing artificial arthrodeses, or for other treatment where new bone formation is desired, further comprises particles of DBM, mineralized bone matrix, CCC, crushed cancellous chips, tricalcium phosphate, hydroxyapatite, or biphasic calcium phosphate dispersed in the matrix.

Typically, particles of DBM or CCC or both are added to the composition or to the tissue graft/implant of the present invention when the composition or implant is being used as a scaffold to obtain bone regeneration or remodeling at the site of implantation. In this embodiment, the mean size of the particles of DBM and mineralized bone matrix are typically from 150 microns to 900 microns, more typically from 250 microns to 800 microns, most typically from 400 to 500 microns. The CCC and crushed cancellous chips are utilized in a larger particle size than the DBM. The mean particle size for CCC is typically 0.5 mm to 5 mm, more typically 1 mm to 3 mm, and even more typically from 1.5 mm to 2.5 mm.

A preferred composition or tissue graft/implant of the present invention that is particularly suited for treating bone trauma, bone disease or bone defects, for providing artificial arthrodeses, or for other treatment where new bone formation is desired, further comprises particles of DBM, mineralized bone matrix, CCC, crushed cancellous chips, tricalcium phosphate, hydroxyapatite, or biphasic calcium phosphate dispersed in the matrix, in combination with a therapeutically effective amount of a growth factor selected from the group consisting of bone morphogenic protein (BMP), LIM mineralization protein (LMP) and RUNX-2.

A preferred growth factor is BMP. The term BMP encompasses a family of well-known naturally occurring proteins (BMP-2, BMP-3, BMP-4, BMP-5, BMP-6, BMP-7, BMP-13 and BMP-14) that are involved in skeletal formation. BMP2 or BMP-2A is a 396 amino acid (aa) dimeric protein in human (chr 20p12) that belongs to the TGF-beta superfamily of structurally related signaling proteins. It is involved in cartilage and bone formation during embryogenesis, but may have additional functions in morphogenesis as implied by its expression in various organs and embryonic tissues. It is abundant in bone, lung, spleen, and colon. Recombinant human BMP-2 (rhBMP-2) consists of two 115 amino acid chains that lack the natural N-terminus and that are bonded by a disulfide bond into a homodimeric protein with an apparent molecular weight of 26 kDa. The rh-BMP-2, lacking the natural N-terminus, has 15–20 times specific activity of the wild-type BMP-2. Methods for isolating BMP from bone are described in U.S. Pat. No. 4,294,753 to Urist and Urist et al., PNAS 371, 1984. Often BMP is obtained by packing fresh fragments of bone into a cavity in an implant that is designed for receiving such packing. However, the amount of BMP in such packing is variable. Therefore, it is preferred that the BMP be a recombinant human BMP such that its activity is known. Recombinant human BMPs are commercially available as described below or prepared as described and known in the art, e.g., in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; WO94/26892 to Celeste et al., and Hogan et al., (1996) Gene Dev., 10:1580–1594; all of which are hereby incorporated herein by reference in their entirety.

BMP3/Osteogenin/BMP-3A is a 472 aa protein in human (chr 4p14-q21), highly expressed in lung, ovary and small intestine. Its function is involved in the cartilage and bone formation. BMP3 and BMP2 genes map to conserved regions between human and mouse. Sequences or methods of isolating BMP-3 are disclosed in Kawabata, M et al. (1998) Cytokine and Growth Factor Reviews 9: 49–61; Ebendal, T et al. (1998), J. Neurosci. Res. 51: 139–146; Reddi, A. H (1998), Nature Biotechnology 16: 247–252; Daluiski, A et al. (2001), Nature Genetics 27: 84; and Bahamonde, M. E et al. (2001) Bone and Joint Surgery 83-A (suppl 1): S156, each of which is incorporated herein by reference.

BMP-3B/GDF-10, a 478 aa protein in human (Chr 10q11.22), belongs to a group of proteins that can induce endochondral bone formation in adult animals, it is closely related in sequence to BMP3 with 44% homology. The amino acid sequences of human and rat BMP-3b precursor proteins are 83% similar, whereas the mature proteins show 98% identity. BMP-3B is mainly expressed in femur, brain, lung, pancreas and testis. Sequences or methods of isolating BMP-3 are disclosed in Hino. J et al. (1996) Biochem Biophysic. Res. Commun. 223 (2), 304–310; Cunningham, N. S. et al. (1995) Growth Factors 12 (2), 99–109; A. H (1998), Nature Biotechnology 16: 247–252; and Daluiski, A. et al. (2001), Nature Genetics 27: 8, each of which is incorporated herein by reference.

BMP4/BMP-2B is a 408 aa protein (Chr 14q22) and vital regulatory molecule that functions throughout development in mesoderm induction, tooth development, limb formation, bone induction, and fracture repair. In human it is expressed in lungs, kidney and is secreted into the extracellular matrix. Sequences or methods of isolating BMP-4 are disclosed in Hogan et al., (1996) Gene Dev., 10:1580–1594; Kawabata, M et al. (1998) Cytokine and Growth Factor Reviews 9: 49–61; Ebendal, T et al. (1998), J. Neurosci. Res. 51: 139–146; Reddi, A. H (1998), Nature Biotechnology 16: 247–252; Daluiski, A et al. (2001), Nature Genetics 27: 84; Bahamonde, M. E et al. (2001) Bone and Joint Surgery 83-A (suppl 1): S156, each of which is incorporated herein by reference.

BMP5 is a 454 aa protein mainly expressed in lungs and liver. (Chr 6). The Bmp5 gene is expressed at the earliest stages of skeletal development in small, local patterns that prefigure the shapes of future skeletal elements. Based upon a high degree of amino acid sequence homology, BMP5, BMP6, and BMP7 constitute a subfamily within the BMPs. Sequences or methods of isolating BMP-5 are disclosed in Kawabata, M et al. (1998) Cytokine and Growth Factor Reviews 9: 49–61, Ebendal, T et al. (1998), J. Neurosci. Res. 51: 139–146; Reddi, A. H (1998), Nature Biotechnology 16: 247–252, each of which is incorporated herein by reference.

BMP6 or VGR1 is a 57 kD protein with 513 aa in human (chr 6p24). Increased production of BMP6 is mediated by the skeletal effects of estrogen on bone and cartilage. BMP-6 differs from other members of the BMP family by its concentration in cartilage of the fetus. Sequences or methods of isolating BMP-6 are disclosed in Kawabata, M et al. (1998) Cytokine and Growth Factor Reviews 9: 49–61; Ebendal, T et al. (1998), J. Neurosci. Res. 51: 139–146; Reddi, A. H (1998), Nature Biotechnology 16: 247–252; and Celeste, A et al. (1990) PNAS. 87: 9843–9847, each of which is incorporated herein by reference.

BMP7 or OP1a 431-amino acid polypeptide (chr 20) that includes a secretory signal sequence, expressed in kidney, bladder and brain. BMP-7 induces cartilage and bone formation. It also plays a role in calcium regulation and bone homeostasis. Sequences or methods of isolating BMP-7 are disclosed in Sampath, T. K et al. (1990) JBC 265: 13198–13205, Reddi, A. H et al. (1998), Nature Biotechnology 16: 247–252; Helder, M. N et al (1995) J. Histochem. Cytochem 43: 1035–1044; and Godin, R. E et al. (1998) Development 125: 3473–3482, each of which is incorporated herein by reference.

BMP13/CDMP-2/GDF-6 is a cartilage derived morphogenetic protein (CDMP) with 436 aa precursor sequence, that is cleaved to a 120 aa polypeptide mature chain. Like all BMPs, it exists as homodimer subunits linked with a disulphide bond. This protein is predominantly expressed in long bones during human embryonic development. Sequences or methods of isolating BMP-13 are disclosed in Chang, S. C et al. (1994) JBC Vol. 269 (45), 28227–28234; Paralkar V. M et al. (1998) JBC 273 (22) 13760–13767; Tomaski S M et al. (1999) Arch Otolaryngol Head Neck Surg. 125 (8) 901–906.

BMP14/CDMP-1/GDF-5 is a 501 aa precursor protein (chr 20q11.2) with a 121 aa mature chain. It is predominantly expressed in long bones during embryonic development and is involved in bone formation. Sequences or methods of isolating BMP-14 are disclosed in Chang, S. C et al. (1994) JBC Vol. 269 (45), 28227–28234; Paralkar V. M et al (1998) JBC 273 (22) 13760–13767; and Tomaski S M et al. (1999) Arch Otolaryngol Head Neck Surg. 125 (8) 901–906, each of which is incorporated herein by reference.

Each of the above described BMP's is commercially available from a variety of sources. Human recombinant BMP-2 is commercially available from a plurality of sources, including Genetics Institute, Inc., Andover, Mass., Abbott Laboratories, North Chicago Ill., and Yamanouchi Pharmaceutical Co., Japan. Recombinant BMP-3 to rBMP-14 are commercially available from Alpha Diagnostics, San Antonio Tex.

The preferred BMPs are recombinant human BMP-2 (rhBMP-2), recombinant human BMP-4 (rhBMP-4), recombinant human BMP-7 (rhBMP-7) and heterodimers thereof. rhBMP-2 is most preferred.

The amino acid sequence of the RUNX-2 protein and vectors suitable for expressing the protein are disclosed in co-pending patent application U.S. Ser. No. 10/437,171, filed May 13, 2003, and incorporated herein in its entirety.

Other suitable tissue growth factors for use in combination with the composition and with the tissue graft/implant of the present invention include transforming growth factor-β (TGF-β), a fibroblast growth factor (FGF) such as FGF-1 to FGF-12, platelet-derived growth factor (PDGF), and insulin-like growth factor (ILGF). All of these factors are well known in the art.

The composition and the tissue graft/implant of the present invention comprise a matrix that is formed from the fibers of defatted, shredded, allogeneic human muscle tissue. This fibrous structure is advantageous because the resulting matrix that is formed is porous and particularly well suited both for the infiltration by colonizing cells, and for the storage and slow release of seeded cells, tissue growth factors (as described above), and chemotactic agents to attract desired cells.

Thus, it is also within the scope of the present invention that the composition or implant/tissue graft of the present invention be combined with seeded cells, a tissue growth factor, or a chemotactic agent, or a combination thereof.

When the composition or tissue graft/implant of the present invention is to be used as a tissue graft for skin, it is optionally seeded with fibroblasts, more typically with fibroblasts, and melanocytes. In this embodiment, it is preferred that the composition or tissue graft further comprise a growth factor suitable for inducing the growth of the fibroblasts and/or melanocytes. Suitable growth factors include a fibroblast growth factor (FGF), such as FGF-1 of FGF-2, epidermal growth factor, transforming growth factor-α (TGF-α), transforming growth factor-β (TGF-β), platelet derived growth factor (PDGF) or a combination thereof. Each of these growth factors are well known in the art and commercially available.

When the composition or tissue graft/implant of the present invention is to be used to treat bone trauma, disease and defects, for artificial arthrodeses and for other treatment where new bone formation is desired, it is optionally seeded with osteogenic cells. Preferably, the composition or tissue graft/implant of the present invention is seeded with stem cells that will provide a natural distribution of the native cells necessary for restoration of the injury or defect at the site of implantation.

The implant/graft of the present invention comprising a matrix of digested allogeneic human muscle was made in various shapes including that of a strip, a sheet, a film, a disk, a molded 3D shaped object, a plug, a sponge, and a gasket. Any of these objects may include a cavity, a pouch, a hole, a post, a hook, or a suture. Any of these objects may be made with or without the addition of DBM, CCC, lyophilized and shredded muscle tissue, collagen fibers, growth factors, antibiotics, stem cells, or other additives.

In making a strip, the dimensions are typically from about 10 mm to 500 mm long, by 10 mm to 200 mm wide and 1 mm to 10 mm thick, more typically from about 15 mm to 200 mm long by 15 mm to 100 mm wide and 2 mm to 8 mm thick, even more typically from about 50 mm to 90 mm long by 15 mm to 35 mm wide and 2 mm to 5 mm thick. The cross section of such a strip may take any shape including a rectangle, square, triangle, other polygon, circle, half circle, ellipse, or partial ellipse.

For a sheet in this embodiment, the dimensions are typically from about 20 mm to 300 mm by 10 mm to 100 mm and 1 mm to 10 mm thick, more typically from about 30 mm to 150 mm by 20 mm to 70 mm and 1.5 mm to 8 mm thick, even more typically from about 50 mm to 100 mm by 25 mm to 50 mm and 2 mm to 5 mm thick.

For a film in this embodiment, the dimensions are typically from about 20 mm to 300 mm by 10 mm to 100 mm and 0.1 mm to 5 mm thick, more typically from about 30 mm to 150 mm by 20 mm to 70 mm and 0.25 mm to 3 mm thick, even more typically from about 50 mm to 100 mm by 25 mm to 50 mm and 0.5 mm to 1 mm thick. A film is characterized by removing most air bubbles prior to or while molding a thin layer of material. The film shape may be flat or may follow a 3D contoured shape. The film may be created in a single layer or by laminating multiple layers of material.

For a disk in this embodiment, the dimensions are typically from about 10 mm to 100 mm diameter and 1 mm to 10 mm thick, more typically from about 30 mm to 80 mm diameter and 2 mm to 8 mm thick, even more typically from about 55 mm to 65 mm diameter and 2.5 mm to 5 mm thick. A disk can be described as a cylinder with nominal diameter greater than nominal height.

For a molded 3D shaped object in this embodiment, the nominal outer body dimensions are typically up to about 100 mm by 100 mm and 25 mm thick, more typically up to about 50 mm by 70 mm and 20 mm thick, even more typically up to about 30 mm by 50 mm and 15 mm thick. A molded 3D shape is typically defined so as to fit into a particular anatomical feature or surgically created space, such as a dental cavity, a drilled tunnel in a bone, or the space between two vertebral bodies in the spine.

For a plug in this embodiment, the dimensions are typically from about 10 mm to 100 mm diameter and 1 mm to 10 mm tall, more typically from about 2 mm to 20 mm diameter and 5 mm to 50 mm tall, even more typically from about 4 mm to 15 mm diameter and 7 mm to 40 mm tall. A plug may be described as a cylinder or extruded 2D shape, such as a square, triangle, star, or polygon, with nominal height greater than nominal diameter or characteristic width of the 2D shape.

For a sponge in this embodiment, the dimensions are typically up to about 500 mm by 500 mm and 50 mm thick, more typically up to about 100 mm by 100 mm and 20 mm thick, even more typically up to about 50 mm by 50 mm and 10 mm thick.

For a gasket in this embodiment, the outside body dimensions are typically up to about 100 mm by 100 mm and 15 mm thick, more typically up to about 50 mm by 50 mm and 5 mm thick, even more typically up to about 25 mm by 25 mm and 2.5 mm thick. The cross section of such a gasket may take any shape including a rectangle, square, triangle, other polygon, circle, half circle, ellipse, or partial ellipse, tracing the entire periphery or some portion of the outside body shape.

It was unexpectedly discovered that the muscle-based implantable composition and tissue graft/implant of the present invention have hemostatic action and cause platelet activation. This is a particular advantage during surgical procedures wherein patient bleeding is always a problem. Thus, the muscle-based implantable composition and tissue graft/implant of the present invention reduce the need for cauterization at the interface between the patient's tissue and the implant.

The muscle-based composition and the tissue graft/implant of the present invention comprise a matrix that is formed from the fibers of defatted, shredded, allogeneic human muscle tissue. Due to the fibrous nature of the muscle tissues, the matrix that is formed is porous and particularly well suited both for the infiltration by colonizing cells, and for the storage and slow release of seeded cells, tissue growth factors, and chemotactic agents that attract a desired cell.

Thus, it is also within the scope of the present invention that the composition or implant/tissue graft of the present invention be combined with a natural or recombinant growth factor to stimulate tissue growth and healing, or a chemotactic agent to attract a desired cell. It is also within the scope of the present invention that the composition or tissue graft/implant of the present invention be seeded with one or more cells prior to implantation into the patient. When the composition or tissue graft/implant of the present invention is to be used as a tissue graft for skin, it is typically seeded with fibroblasts, preferably with melanocytes. When the composition or tissue graft/implant of the present invention is to be used to treat a defect or an injury to a bone, it is seeded with osteogenic cells. Preferably, when the composition or tissue graft/implant of the present invention is to be used to treat any tissue defect or injury, it is seeded with stem cells that will provide the native cells necessary for restoration of the injury or defect.

The tissue grafts and implants of the present invention exhibit a great degree of tensile strength. They are readily stitchable and retain a majority of their tensile strength even when rehydrated. In addition, upon hydration, tissue grafts and implants of the present invention are moldable and suitable for filling in irregular gaps or holes in the tissue to be repaired. Typically, the hydrated tissue is press fitted by the surgeon into the defect or cavity to be filled.

The implantable compositions and tissue grafts/implants of the present invention are formed from an intermediate composition comprising a muscle tissue slurry that is poured into a mold for formation into of a composition or tissue graft/implant of any size or shape. As noted above, the muscle tissue slurry can be combined with other agents, such as DBM, CCC or a collagen (e.g., tendon, fascia) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable shape is then ready for packaging and final sterilization.

In its second aspect, the present invention is directed to a method for making a (muscle-based) composition or a tissue implant suitable for treating an injury or a surgical or medical condition in a human patient, wherein the tissue implant comprises a matrix of digested allogeneic human muscle. In this embodiment, the method comprises the steps of:

i. removing the fat and soluble proteins from allogeneic or xenogeneic mammalian muscle tissue;
ii. lyophilizing the muscle tissue from step (i);
iii. shredding the lyophilized muscle tissue;
iv. mixing the shredded muscle tissue in an aqueous carrier to form a muscle tissue slurry having a viscosity within the range of 1 centistoke to 20,000 centistokes;
v. transferring the muscle tissue slurry to an appropriate shaped mold; and
vi. drying the slurry in the mold to form the correspondingly shaped tissue implant.

In the above method, the matrix of digested allogeneic human muscle comprises from about 1% to about 100% of the final weight of the composition or implant, more typically from 50% to about 99% of the final weight of the implant, even more typically from 75% to about 99% of the final weight of the implant.

The muscle tissue slurry that is used to make the composition and implant of the present invention is the subject of copending parent application, U.S. Ser. No. 10/754,310, filed Jan. 9, 2004, and incorporated herein by reference in its entirety. The muscle tissue slurry has a viscosity within the range of 1 centistoke to 20,000 centistokes when measured at 25° C. Typically, the muscle tissue slurry has a viscosity within the range of 1 centistoke to 10,000 centistokes when measured at 25° C.; more typically, the muscle tissue slurry has a viscosity within the range of 1 centistoke to 5,000 centistokes when measured at 25° C.

The muscle tissue slurry that is used to make the composition and/or tissue graft/implants of the present invention is also characterizable in terms other than viscosity. Specifically, the muscle tissue slurry is characterized instead by the ratio of the volume of aqueous carrier (milliliters) to dry weight of muscle (grams). The aqueous carrier is acidic, basic or neutral. Preferably, the aqueous carrier is an aqueous acidic solution ("an acid"). Typically, the ratio of acid (volume) to dry weight of muscle (grams) is within the range of 100:1 to 10:1; more typically within the range of 80:1 to 20:1; most typically within the range of 70:1 to 30:1. The choice of the ratio of acid to protein determines the viscosity of the slurry and the choice is based upon the ultimate application of the slurry. The muscle tissue slurry of the present invention was used to make the various tissue implants and grafts (collectively "implants") disclosed further herein.

The viscosity of the muscle tissue slurry (i.e., intermediate composition) ranges between slightly greater than the viscosity of water to almost solid.

Although autogeneic muscle can be used in the intermediate composition of the present invention, the source of the muscle is typically donor muscle that is obtained from cadavers and thus, the muscle is allogeneic. While the present invention is discussed herein in terms of an allogeneic human muscle source and being used for preparing a tissue implant for humans, any non-human mammal may be used as the muscle donor and the resulting slurry used to prepare a xenogeneic implant for use in a human or in another species of mammal. Preferred xenogeneic muscle sources are porcine and bovine. Pigs are currently being used to generate minimally antigenic hearts suitable for implantation as living heart transplants in humans. In the examples herein, the applicants disclose that they ectopically implanted into a rat a tissue matrix (in the form of a sponge) that was derived from human donor muscle and the tissue matrix was resorbed over a period of time without inducing an inflammatory response. This establishes the functionality of the tissue matrix as a biocompatible resorbable tissue scaffold even when implanted (as a xenograft) in a different species. Thus, there is evidence that the intermediate composition of the present invention would produce an acceptable tissue matrix even when made from xenograft muscle tissue.

In a preferred embodiment of the present invention, the muscle tissue is defatted prior to or after being shredded. Preferably, it is defatted prior to being shredded. In this embodiment, the donor muscle is cut into chunks of sufficiently small size (e.g., 20 mm×20 mm) to allow the tissue to be easily defatted. Suitable methods for defatting tissue are well known in the art. Typically, this involves treating the tissue with a fat dissolving substance such as 60% to 90% alcohol in water. See U.S. Pat. No. 5,846,484, entitled "Pressure flow system and method for treating a fluid permeable workpiece such as a bone," which issued to Scarborough, et al. on Dec. 8, 1998. In the present case, the applicants utilized the assignees' well known method for defatting tissue, which also has the added benefit of removing blood, cellular debris, and soluble and antigenic proteins, by subjecting the muscle tissue to alternating cycles of pressure and vacuum in the sequential presence of solvents, such as isopropyl alcohol, hydrogen peroxide and a detergent. These methods are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety.

In a more preferred embodiment, the defatted allogeneic human muscle tissue was dried, more preferably by lyophilization, to facilitate further processing, such as shredding. The lyophilization process need not remove all of the water. While the water content of the chopped allogeneic muscle can vary, it is typically dried to about 3% moisture content by weight. It is especially preferred that the allogeneic human muscle tissue be defatted prior to lyophilization.

The defatted and dried muscle tissue was shredded to a coarse fiber. Shredding is accomplished by any commercial shredder. Suitable shredders include coffee grinders, food processors, and the like.

The shredded muscle tissue was mixed vigorously with a biocompatible acid to produce the muscle slurry that is the intermediate composition of the present invention. On a small scale, mixing was accomplished with a hand-held food processor. Mixing takes from 15 seconds to over two minutes and is dependent upon the amount of shredded protein and the volume of acid. Mixing should continue until the slurry has uniform consistency. After mixing, the slurry is preferably degassed. Degassing was accomplished by centrifugation, or possibly vacuum centrifugation.

The biocompatible acid is either a biocompatible organic acid or a biocompatible inorganic acid. Preferably, a suitable biocompatible acid is selected from the group consisting of acetic acid, citric acid, formic acid, hydrochloric acid, lactic acid, phosphoric acid, phosphorus acid and sulfuric acid. More preferably, the biocompatible acid is an organic acid; most preferably the organic acid is acetic acid. The function of the acid is to partially digest the muscle tissue.

The intermediate composition employed in the present invention is implantable in liquid form, such as by injecting into the patient at a site in need of restoration. In another embodiment, it is dried to a predetermined shape to prepare a variety of tissue implants.

Thus, the present invention is directed to a tissue graft of implant suitable for treating an injury or a surgical or medical condition in a human patient, wherein the tissue implant comprises a matrix of digested allogeneic human muscle. In this embodiment, the matrix of digested allogeneic human muscle comprises from about 1% to about 100% of the dry weight of the implant, more typically from 15% to about 95% of the dry weight of the implant, even more typically from 25% to about 85% of the dry weight of the implant.

In another embodiment, the method of making a composition or tissue implant of the present invention further comprises combining the allogeneic human muscle with a demineralized bone matrix (DBM), mineralized bone matrix, cortical cancellous chips (CCC), crushed cancellous chips, tricalcium phosphate, hydroxyapatite, or biphasic calcium phosphate and/or shredded allogeneic human tendon. The addition of any of these components increases the viscosity of the intermediate slurry. When the tissue implant of the present invention contains DBM, mineralized bone matrix, CCC, crushed cancellous chips, tricalcium phosphate, hydroxyapatite, or biphasic calcium phosphate or a combination thereof, the resulting tissue implant is osteogenic and particularly suited for repairing bone. The implant of this embodiment also exhibits improved dimensional stability and ability to hold shape during drying, rehydration and handling. In one variation of the above embodiment, the DBM, mineralized bone matrix, CCC, crushed cancellous chips, tricalcium phosphate, hydroxyapatite, or biphasic calcium phosphate or a combination thereof are dispersed equally or randomly throughout the matrix. In another variation, the DBM, mineralized bone matrix, CCC, crushed cancellous chips, or both are sandwiched between layers of the matrix to form a laminate implant. In either of the above referenced embodiments, the DBM, mineralized bone matrix, CCC, crushed cancellous chips, tricalcium phosphate, hydroxyapatite, or biphasic calcium phosphate or a combination thereof typically constitute from 1% to 99%, more typically from 50% to 99%, most typically from 90% to 99% of the dry weight of the composition or implant.

When the tissue implant contains tendon, it is tougher and stronger than the digested human muscle matrix alone and is particularly suited as a dressing for a wound or burn that will become infiltrated with skin cells and allow for development of a replacement skin layer that will cover the wound or burn. The ratio of tendon to intermediate composition ranges from 1:99 to 99:1 by dry weight. Typically, the range is 10:90 to 90:10; more typically, the range is 25:75 to 75:25. While the above discussion is in relation to "tendon," which is a preferred source of collagen for this invention, it is intended that any collagen source be used, including tendon, fascia and dermis.

After the mixing step, the resulting intermediate composition (the digested allogeneic human muscle slurry) of the present invention is optionally degassed, by pouring the slurry into plates or tubes, and centrifuging them to eliminate any entrapped air and produce a higher density slurry.

Alternatively, the slurry is poured into a mold for formation of an implantable tissue matrix of any size or shape. As noted above, the slurry can be combined with other agents, such as DBM, CCC or a collagen (e.g., tendon, fascia) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable film or shape is then ready for packaging and final sterilization.

Prior to implantation, the freeze dried composition, tissue graft or implant of the present invention is removed from its sterile packaging and rehydrated by contacting them with water, saline, blood, plasma, a buffered solution, or any other suitable liquid. Preferably, the rehydrating liquid contains a growth factor or a chemotactic agent as discussed above.

In a pilot study, prototype implants were resorbed into an ectopic site in an athymic nude rat model, without any signs of an inflammatory response. Specifically, an implant of Example 2, containing 20% DBM was implanted in abdominal muscle pouches of athymic nude rats using a modified Urist model. Urist, M. R., "Bone: Formation by Autoinduction," Science 160:893–894 (1965). The explants were retrieved four weeks later, processed, and evaluated histologically for evidence of new bone formation. The control implants containing only the sponge carrier were resorbed without evidence of inflammation. More significantly, the implants containing DBM demonstrated signs of new bone formation (endochondral ossification). Hence, the muscle tissue matrix of the present invention, under the influence of DBM, provided scaffolding for colonization by native restorative cells and the laying down of new bone.

Alternatively, the slurry is poured into a mold for formation of an implantable tissue matrix of any size or shape. As noted above, the slurry can be combined with other agents, such as DBM, mineralized bone matrix, CCC, crushed cancellous chips, or a collagen (e.g., tendon, fascia, or dermis) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable film or shape is then ready for packaging and final sterilization.

Several parameters are controlled during the molding process which impact the shape, composition, and material properties of the finished grafts. Shrinkage of the material during drying is noted, especially as characteristic thickness and bulk of the implant increase. Shrinkage results in changes in shape, density, uniformity, thickness, appearance, and residual stresses of the implants. Shrinkage and its effects can be controlled and manipulated by careful control of parameters including drying time, thickness of implant sections, shape of implant, coring or segmenting of thick sections, and shape and configuration of molds. Other process parameters directly affecting the finished product include order of process steps, spatial orientation of the graft during processing, and method of application of the slurry into the molds. For example, freezing before drying creates a thicker sponge implant with porous structure, where drying without freezing produces a compressed and much thinner film from a similar amount of graft material. Gravitational effects can produce grafts with material either concentrated in a particular area or spread more evenly throughout the mold. Thus, rotational molding can produce thin film grafts wrapped evenly around complex internal or external 3D molds, nominal drying under constant gravitational force can produce grafts which are slightly thicker at the bottom due to slow flowing of the slurry during drying, and drying in a vacuum centrifuge can produce grafts with material strongly concentrated in the direction of the centrifugal forces. Finally, different graft properties can be created by introducing the slurry to a given mold all at once in order to form a uniform implant, or by introducing it in layers or stages and allowing for drying or adding additional materials between layers to produce a layered composite or fiberglass like structure.

Thus, in another embodiment, the present invention is directed to a method for making the intermediate composition (muscle tissue slurry) of the present invention comprising the steps of:

i. removing the fat and soluble proteins from allogeneic or xenogeneic mammalian muscle tissue;
ii. lyophilizing the muscle tissue from step (i);
iii. shredding the lyophilized muscle tissue; and
iv. mixing the shredded muscle tissue in an aqueous carrier to form a muscle tissue slurry having a viscosity within the range of 1 centistoke to 20,000 centistokes.

The tendon that is used in the tissue implants of the present invention is processed the same as the allogeneic human muscle. It is chopped into pieces, defatted, freeze dried (lyophilized), shredded into a coarse fiber, and acid digested to provide a viscous tendon digestate that is suitable for combining with the acid digested allogeneic muscle (intermediate composition) of the present invention. The ratio of tendon digestate to intermediate composition ranges from 1:99 to 99:1. Typically, the range is 10:90 to 90:10; more typically, the range is 25:75 to 75:25. While the above discussion is in relation to "tendon," which is a preferred source of collagen for this invention, it is intended that any collagen source be used, including fascia. The collagen source is xenogeneic or allogeneic. Preferably, it is allogeneic.

EXAMPLE 1

Preparation of a Slurry of Allogeneic Human Muscle

Skeletal muscle was removed from a donor cadaver and cut into chunks (20 mm×20 mm). The chunks of skeletal muscle were defatted, deantigenized and soluble protein was removed by subjecting the muscle tissue to cyclically alternating pressure and vacuum in the sequential presence of the isopropyl alcohol, hydrogen peroxide and a detergent. The method is fully described in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety. After the above cleansing process, the defatted and non-antigenic muscle tissue was lyophilized to remove the moisture. The lyophilization procedure was a standard 17-hour program. The dried chunks were shredded and chopped in a grinder. The processing time varied from 5 seconds to 2 minutes depending upon the amount of lyophilized muscle being processed, dryness and starting size. At this stage, the shredded muscle tissue looks like fluffed fibers. The shredded muscle tissue were weighed and then combined with a predetermined amount of 10% or 20% aqueous acetic acid according to the table below:

TABLE 1

Ratios of Acetic Acid (ml) to weight of dry muscle (g)

| Acid | Muscle (g) Acid:muscle | Muscle (g) Acid:muscle | Muscle (g) Acid:muscle |
|---|---|---|---|
| 10% acetic acid | 0.5 g 46:1 | 0.75 g 34:1 | 1 g 22:1 |
| 20% acetic acid | 0.5 g 46:1 | 0.75 g 34:1 | 1 g 22:1 |

The combined acid solution and muscle tissue were mixed with a high speed mixer until a uniform gel (i.e., slurry) was formed. Mixing took between 15 seconds to more than 2 minutes depending upon the acid concentration, amount of muscle tissue and volume of acid solution.

The above described slurry was used alone or combined with another component to make a tissue implant of the present invention. The lower viscosity (more dilute) slurries were preferred when making pourable/flowable films. The lower to intermediate viscosity slurries were more desirable when being combined with DBM or CCC or tendon, each of which thickened the slurry.

EXAMPLE 2

Formulation Comprising the Slurry of Example 1 and DBM

The slurry of Example 1 was degassed via centrifugation. After the degassing, the slurry was transferred to a mixing bowl. DBM was added and mixed to uniformity at ratios of 0.1%, 1%, 5%, 10%, 20% and 30% (DBM weight to slurry weight).

A portion of each of the above slurries containing the DBM were poured into molds and allowed to dry at room temperature with positive airflow. The dried products produced a series of muscle based tissue implants in the form of films with the differing amounts of DBM embedded therein.

A second portion of the slurries from above was poured into molds, frozen, and lyophilized. The dried products produced a series of sponge-like tissue implants having increasing amounts of DBM therein.

EXAMPLE 3

Formulation Comprising the Slurry of Example 1 and CCC

The slurry of Example 1 was degassed via centrifugation. After the degassing, the slurry was transferred to a mixing bowl. CCC was added and mixed until uniform at a ratio of 50% (CCC volume to slurry volume). The slurry containing CCC was poured into a mold, frozen, and lyophilized. This dried product produced a tissue implant in the form of a sponge with CCC imbedded therein.

The degassed slurry from above was transferred to a mixing bowl, where 60% CCC (CCC volume to slurry volume) and 10% DBM (DBM volume to slurry volume) were added to the degassed slurry with mixing. Mixing continued until a uniform appearing mixture was formed. The slurry was poured into a cube shaped mold, frozen, and lyophilized. This dried product produced a cube shaped tissue implant having CCC and DBM imbedded therein.

EXAMPLE 4

Formulation Comprising the Slurry of Example 1 and A Slurry of Tendon

The slurry from Example 1 was degassed via centrifugation. After degassing, the slurry was transferred to a series of three (3) mixing bowls. Using allogeneic human tendon, a tendon slurry was made in the exact same manner as the muscle slurry. After the solubilized tendon slurry was degassed, a portion of it was added to each of the three (3) mixing bowls. The ratio of muscle to tendon in each of the three (3) bowls was 25:75, 50:50 and 75:25 (muscle volume: tendon volume), respectively. A portion of the tendon/skeletal slurry mixtures were poured into flat molds and allowed to dry at room temperature with positive airflow. Once dried, the three dried materials each produced a tissue implant in the form of a film.

Three identical tendon/skeletal muscle slurries were poured into molds, frozen, and lyophilized. The lyophilized frozen slurries produced tendon/skeletal muscle based implants in the form of a sponge.

EXAMPLE 5

Preparation of an Implantable Strip

A series of implantable strips were created from the films produced in Examples 1, 2, 3, and 4. Specifically, the dried films were cut into implantable strips that were 0.5 mm thick, 20 mm wide, and 70 mm long.

EXAMPLE 6

Preparation of an Implantable Sheet

An implantable sheet was created from the films produced in Example 1, 2, 3, and 4. The dried films either were left in the final shape of their molds, or were cut into sheets that were 0.5 mm thick, 70 mm wide and 70 mm long. Sheets were made that were also three dimensional, such as convex and concave spherical bodies. These implantable three dimensional films were made via rotational molding, vacuum centrifugation drying, room temperature drying, or room temperature drying with forced air, to a thin film in a three dimensional mold. Thicker sheets were produced in both two dimensional and three dimensional forms by successive reapplication of muscle tissue slurry, after drying of the preceding layer. In some cases DBM was added to the implant between this application of successive layers, to create a laminated tissue implant impregnated with DBM.

EXAMPLE 7

Preparation of an Implantable Sponge

A series of implantable sponges were made as specified in Examples 1, 2, 3, and 4 above. Using appropriate molds, the sponges were made in a square, circular, or hexagonal forms. The average thickness was 5 mm. The squares were as large as 50 mm by 50 mm. The circles had diameters as large as 90 mm. The hexagons were 40 mm per side.

EXAMPLE 8

Preparation of an Implantable Gasket

Using the slurry of Example 1, a gasket was made as a thinner version (2.5 mm) of the sponge in Example 7. The gasket was used in conjunction with a bone plate to tie together two model vertebral bodies in the laboratory.

EXAMPLE 9

Preparation of a Graftable Wound Dressing

The films from Example 4 were suitable for use as a wound dressing/skin graft. The films are hydrated before use with sterile saline until soft and pliable and then applied to the wound. Any excess film overhanging the wound is cut off with surgical scissors.

EXAMPLE 10

Biological Activity of an Ectopically Implanted Sponge in a Rat

The implant of Example 2, containing 20% DBM, and measuring about 5 mm diameter by about 25 mm length, was implanted in abdominal muscle pouches of athymic nude rats using a modified Urist model. Urist, M. R., "Bone: Formation by Autoinduction," Science 160:893–894 (1965). Explants were retrieved four weeks later, processed, and evaluated histologically for evidence of new bone formation. Whereas control implants containing only the sponge carrier were resorbed without evidence of inflammation, those containing DBM demonstrated signs of new bone formation (endochondral ossification).

EXAMPLE 11

Composite Implants for Hip Replacement Applications

An implant following the method of Example 2, containing 20% DBM, was poured into molds shaped to match an existing metal hip replacement stem graft and an acetabular cup. The hip stem graft was structurally enhanced with pieces of bone and bone fragments placed into the material during molding. The acetabular cup graft featured a two part construction, wherein a sponge implant section was formed inside of and bonded to an earlier formed, shaped three dimensional thin film mold. No attempt was made to quantify the failure load or strength of the implants, but the proof of concept objective was satisfied as the stem and cup implants both withstood normal handling and manipulation.

EXAMPLE 12

Meniscus Replacement Implant

An implant following the method of Example 2, containing no DBM or DBM added only to specific regions of the graft, is proposed as meniscus replacement graft. The combination of precisely controlled shaping and contouring with appropriate load bearing capacity and appropriate remodeling response with or without the application of specific growth factors to various parts of the graft answers a unique need in the art.

EXAMPLE 13

Precise Anatomically Matched Implants

An implant following the method of Example 2, can be formed in a mold created by known methods from digitized data of an area in need of treatment. Methods of mold creation are known in the art, and can include x-ray, ultrasound, or cat-scan imaging data translated to a computer aided design (CAD) or computer aided manufacturing (CAM) or computer numerical controlled (CNC) machining center. The implants made from these methods could be used to treat conditions where exact matching of the anatomical structure is critical and where a biocompatible allograft implant is beneficial. Applications can include facial reconstruction, general orthopedic defects and bone segment replacements, and vertebral body replacements.

EXAMPLE 14

Flowable Implants

An implant following the method of Example 2 was transferred to a syringe after drying and full rehydration in sterile saline solution. The rehydrated implant was found to be flowable under the forces of the syringe, and could be placed in rows or used to fill cavities similar to those found commonly in surgical sites. A second flowable implant was created by transferring the slurry of Example 1 directly into a syringe and then using the syringe to flow the graft material into rows or into cavities similar to those found commonly in surgical sites.

EXAMPLE 15

Moldable Implants

An implant following the method of Example 2 was partially rehydrated with sterile saline solution after drying. The implant was placed into a cavity and molded to the shape of the cavity under manual manipulation. The implant molded to the shape of the cavity and then retained that shape under minimal forces including gravity and light rinsing.

The invention claimed is:

1. A composition comprising a matrix suitable for implantation in humans, said matrix comprising a dried aqueous slurry of shredded, allogeneic human muscle tissue.

2. The composition of claim 1, wherein said muscle tissue is striated muscle tissue.

3. The composition of claim 2, wherein said striated muscle tissue is skeletal muscle.

4. The composition of claim 1, wherein said shredded allogeneic human muscle tissue is also defatted.

5. The composition of claim 1, wherein said shredded allogeneic human muscle tissue was also lyophilized prior to shredding.

6. The composition of claim 1, further comprising a particulate component selected from the group consisting of demineralized bone matrix (DBM), mineralized bone matrix, cortical cancellous chips (CCC), crushed cancellous chips, tricalcium phosphate, hydroxyapatite, biphasic calcium phosphate and combinations thereof.

7. The composition of claim 6, wherein the particulate component constitutes from 50% to 99% of the dry weight of the composition.

8. The composition of claim 7, wherein the particulate component constitutes from 90% to 99% of the dry weight of the composition.

9. The composition of claim 1, further comprising an amount effective for forming new bone of a bone morphogenic protein (BMP), a LIM mineralization protein, or RUNX-2 protein.

10. The composition of claim 9, wherein said BMP is selected from the group consisting of BMP-2, BMP-4 and BMP-7.

11. The composition of claim 10, wherein said BMP is BMP-2.

12. The composition of claim 11, wherein said BMP-2 is a recombinant human BMP-2.

13. An implant suitable for implantation in humans comprising a matrix of defatted, shredded, allogeneic human muscle tissue that has been combined with an aqueous carrier and dried into a predetermined shape.

14. The implant of claim 13, wherein said muscle tissue is striated muscle tissue.

15. The implant of claim 14, wherein said striated muscle tissue is skeletal muscle.

16. The implant of claim 13, wherein said shredded allogeneic human muscle tissue is also defatted.

17. The implant of claim 13, wherein said shredded allogeneic human muscle tissue was also lyophilized prior to shredding.

18. The implant of claim 13, further comprising a particulate component selected from the group consisting of demineralized bone matrix (DBM), mineralized bone matrix, cortical cancellous chips (CCC), crushed cancellous chips, tricalcium phosphate, hydroxyapatite, biphasic calcium phosphate and a combination thereof.

19. The implant of claim 18, wherein the particulate component constitutes from 50% to 99% of the dry weight of the implant.

20. The implant of claim 19, wherein the particulate component constitutes from 90% to 99% of the dry weight of the implant.

21. The implant of claim 13, further comprising an amount effective for forming new bone of a bone morphogenic protein (BMP), a LIM mineralization protein, or RUNX-2 protein.

22. The implant of claim 21, wherein said BMP is selected from the group consisting of BMP-2, BMP-4 and BMP-7.

23. The implant of claim 22, wherein said BMP is BMP-2.

24. The implant of claim 23, wherein said BMP-2 is a recombinant human BMP-2.

25. The implant of claim 13, wherein said matrix of digested allogeneic human muscle comprises from about 1% to about 100% of the final weight of said implant.

26. The implant of claim 25, wherein said matrix of digested allogeneic human muscle comprises from 25% to about 85% of the weight of said tissue implant.

27. The implant of claim 18, wherein said particulate component is DBM.

28. The implant of claim 27, wherein said DBM is uniformly distributed throughout the matrix.

29. The implant of claim 27, wherein said DBM is layered within said matrix.

30. The implant of claim 18, wherein said particulate component is CCC.

31. The implant of claim 30, wherein said CCC is uniformly distributed throughout the matrix.

32. The implant of claim 30, wherein said CCC is layered within said matrix.

33. The implant of claim 13 further comprising digested allogeneic human tendon.

34. A method for making an implantable tissue comprising the steps of:
   i. removing the fat and soluble proteins from allogeneic or xenogeneic mammalian muscle tissue;
   ii. lyophilizing the muscle tissue from step (i);
   iii. shredding the lyophilized muscle tissue;
   iv. mixing the shredded muscle tissue in an aqueous carrier to form a muscle tissue slurry having a viscosity within the range of 1 centistoke to 20,000 centistokes;
   v. transferring the muscle tissue slurry to an appropriate shaped mold; and
   vi. drying the slurry in the mold to form the tissue implant having the corresponding shape of said mold.

35. The method of claim 24, wherein the tissue implant is a shaped sponge.

* * * * *